(12) United States Patent
Dieckgraefe

(10) Patent No.: US 7,915,235 B2
(45) Date of Patent: Mar. 29, 2011

(54) HIGH AFFINITY LIGANDS BIND TO CLOSTRIDIUM DIFFICILE TOXIN A

(76) Inventor: Brian Dieckgraefe, Chesterfield, MO (US)

( * ) Notice: Subject to any disclaimer, the term of this patent is extended or adjusted under 35 U.S.C. 154(b) by 10 days.

(21) Appl. No.: 11/716,052

(22) Filed: Mar. 9, 2007

(65) Prior Publication Data

US 2007/0249524 A1    Oct. 25, 2007

Related U.S. Application Data

(60) Provisional application No. 60/783,442, filed on Mar. 20, 2006.

(51) Int. Cl.
*A61K 31/715* (2006.01)
(52) U.S. Cl. .......................... 514/61; 536/123
(58) Field of Classification Search .................. 514/61; 536/123
See application file for complete search history.

(56) References Cited

U.S. PATENT DOCUMENTS

| | | | | |
|---|---|---|---|---|
| 5,635,606 | A * | 6/1997 | Heerze et al. | 530/412 |
| 6,692,732 | B2 | 2/2004 | Fitzpatrick et al. | |
| 6,890,523 | B2 | 5/2005 | Kurtz et al. | |
| 2005/0214246 | A1 | 9/2005 | Mhaskar et al. | |
| 2006/0029568 | A1 | 2/2006 | Kurtz et al. | |

FOREIGN PATENT DOCUMENTS

WO    WO 9305803 A1 *  4/1993

OTHER PUBLICATIONS tables for Mammalian Plate Array Version 3.8, http://www.functionalglycomics.org, accessed online on Jan. 20, 2010.*
Kitagawa et al. Biochemistry, 1991, 30, p. 2869-2876.*
Schiller et al. Digestive Diseases and Sciences, 1997, 42(1), p. 1-5.*
Frank et al. Nature Reviews, 2003, 2, p. 566-580.*
Castagliuolo et al. Gastroenterology 1996, 111, p. 433-438.*
U. J. Nilsson et al., "Immobilization of Reducing Sugars as Toxin Binding Agents," *Bioconjugate Chem.* 1997, 8, pp. 466-471.
William Braunlin et al., "Toxin Binding of Tolevamer, a Polyanionic Drug That Protects Against Antibiotic-Associated Diarrhea," *Biophysical Journal*, Jul. 2204, vol. 87, pp. 534-539.
Kenneth D. Tucker et al., "Toxin A of *Clostridium Difficile* Binds to the Human Carbohydrate Antigens, I, X, and Y," *Infection and Immunity*, Jan. 1991, pp. 73-78.
Jason G. S. Ho et al., "Crystal Structure of Receptor-Binding C-Terminal Repeats from *Clostridium Difficile* Toxin A," PNAS, Dec. 20, 2005, vol. 102, No. 51, pp. 18373-18378.

* cited by examiner

*Primary Examiner* — Shaojia Anna Jiang
*Assistant Examiner* — Jonathan S Lau
(74) *Attorney, Agent, or Firm* — Banner & Witcoff, Ltd

(57) ABSTRACT

Glycans are identified which have high affinity for *C. difficile* toxin A. They share one of two saccharide backbones and may have additional side chains. The backbones are galactose-β1-3 N-acetyl-D-glucosamine-β-1-3-galactose-β-1-4-N-acetyl-D-glucosamine and galactose-α-1-3-galactose-β-1-4-N-acetyl-D-glucosamine. The ligands may be used therapeutically, prophylactically, and diagnostically.

22 Claims, 11 Drawing Sheets

FIGURE 1

C. Difficile toxin A binding carbohydrates

Figure 2.

| Glycan No. | Glycan Name | Avg. RFU | SEM |
|---|---|---|---|
| 116 | Galb1-3(Fuca1-4)GlcNAcb1-3Galb1-4GlcNAcb-Sp0 | 29098 | 1164 |
| 218 | NeuAca2-3Galb1-3(Fuca1-4)GlcNAcb1-3Galb1-4(Fuca1-3)GlcNAcb-Sp0 | 14911 | 473 |
| 224 | NeuAca2-3Galb1-3GlcNAcb1-3Galb1-4GlcNAcb-Sp0 | 4435 | 362 |
| 3 | AGP-B (AGP ConA bound) | 3628 | 465 |
| 103 | Galα1-3Galβ1-4(Fucα1-3)GlcNAcβ–Sp8 | 1814 | 961 |
| 24 | (Galβ1-4GlcNAcβ)$_2$-3,6-GalNAcα–Sp8 | 1530 | 1511 |
| 130 | Galβ1-3Galβ–Sp8 | 1360 | 1314 |
| 229 | Neu5Acα2-3Galβ1-4(Fucα1-3)GlcNAcβ1-3Galβ1-4(Fucα1-3)GlcNAcβ1-3Galβ1-4(Fucα1-3)GlcNAcβ–Sp0 | 982 | 927 |
| 133 | Galβ1-3GlcNAcβ–Sp0 | 929 | 892 |
| 96 | Gala1-3(Fuca1-2)Galb1-4(Fuca1-3)GlcNAcb-Sp0 | 789 | 145 |
| 6 | Transferrin | 580 | 154 |
| 4 | Ceruloplasmin | 475 | 89 |
| 80 | GalNAca1-3(Fuca1-2)Galb1-4(Fuca1-3)GlcNAcb-Sp0 | 327 | 89 |
| 1 | Alpha1-acid glycoprotein (AGP) | 324 | 18 |
| 187 | KDNα2-3Galβ1-3GlcNAcβ–Sp0 | 269 | 228 |
| 135 | Galβ1-4(Fucα1-3)GlcNAcb–Sp0 | 218 | 157 |
| 137 | Galb1-4(Fuca1-3)GlcNAcb1-4Galb1-4(Fuca1-3)GlcNAcb-Sp0 | 197 | 41 |
| 82 | GalNAcα1-3(Fucα1-2)Galβ1-4GlcNAcβ–Sp8 | 188 | 76 |
| 105 | Galα1-3Galβ1-4GlcNAcβ–Sp8 | 172 | 67 |

Figure 3A

| Glycan No. | Glycan Name | Avg. RFU | SEM |
|---|---|---|---|
| 34 | [3OSO3]Galβ1-4(Fucα1-3)GlcNAcβ–Sp8 | 171 | 72 |
| 81 | GalNAcα1-3(Fucα1-2)Galb1-4GlcNAcb-Sp0 | 169 | 36 |
| 2 | AGP-A (AGP ConA flowthrough) | 151 | 16 |
| 140 | Galβ1-4[6OSO3]Glcβ–Sp8 | 134 | 71 |
| 136 | Galβ1-4(Fucα1-3)GlcNAcb–Sp8 | 122 | 19 |
| 219 | Neu5Acα2-3Galβ1-3(Neu5Acα2-3Galβ1-4)GlcNAcβ-Sp8 | 122 | 50 |
| 233 | Neu5Acα2-3Galb1-4(Fucα1-3)GlcNAcb1-3Galb1-4GlcNAcb-Sp8 | 113 | 35 |
| 223 | NeuAcα2-3Galb1-3GalNAcb1-3Galα1-4Galb1-4Glcb-Sp0 | 110 | 70 |
| 163 | GlcNAcb1-3Galb1-3GalNAcα-Sp8 | 105 | 33 |
| 36 | [3OSO3]Galβ1-4GlcNAcβ–Sp0 | 104 | 17 |
| 28 | [3OSO3]Galb1-4Glcb-Sp8 | 102 | 66 |
| 100 | Galα1-3(Galα1-4)Galb1-4GlcNAcb-Sp8 | 96 | 56 |
| 145 | Galb1-4GlcNAcb1-3Galb1-4(Fucα1-3)GlcNAcb1-3Galb1-4(Fucα1-3)GlcNAcb-Sp0 | 94 | 25 |
| 97 | Galα1-3(Fucα1-2)Galb1-4GlcNAc-Sp0 | 93 | 24 |
| 188 | KDNα2-3Galβ1-4GlcNAcβ–Sp0 | 93 | 22 |
| 72 | Fucα1-2Galβ1-4GlcNAcβ–Sp8 | 92 | 24 |
| 118 | Galβ1-3(Fucα1-4)GlcNAc–Sp8 | 91 | 11 |
| 66 | Fucα1-2Galb1-4(Fucα1-3)GlcNAcb1-3Galb1-4(Fucα1-3)GlcNAcb1-3Galb1-4(Fucα1-3)GlcNAcb-Sp0 | 90 | 32 |
| 43 | [6OSO3]Galβ1-4Glcβ–Sp8 | 89 | 34 |
| 67 | Fucα1-2Galb1-4(Fucα1-3)GlcNAcβ–Sp0 | 88 | 19 |
| 18 | β-D-Glc–Sp8 | 88 | 32 |
| 26 | [3OSO3][6OSO3]Galb1-4[6OSO3]GlcNAcb-Sp0 | 86 | 34 |
| 30 | [3OSO3]Galβ1-4(6OSO3)Glcβ–Sp8 | 86 | 26 |
| 83 | GalNAcα1-3(Fucα1-2)Galb1-4Glcb-Sp0 | 85 | 57 |
| 144 | Galβ1-4GlcNAcβ1-3GalNAcα–Sp8 | 85 | 12 |
| 33 | [3OSO3]Galβ1-3GlcNAcβ–Sp8 | 84 | 21 |
| 253 | Neu5Acα2-8Neu5Acα2-3Galβ1-4Glcβ–Sp0 | 83 | 34 |
| 107 | Galα1-3Galβ–Sp8 | 79 | 14 |

Figure 3B

| | | | |
|---|---|---|---|
| 54 | Neu5Aca2-3Galb1-4GlcNAcb1-2Mana1-3(Neu5Aca2-3Galb1-4GlcNAcb1-2Mana1-6)Manb1-4GlcNAcb1-4GlcNAcb-Sp8 | 78 | 32 |
| 11 | α-L-Fuc–Sp8 | 78 | 18 |
| 134 | Galβ1-3GlcNAcβ–Sp8 | 75 | 16 |
| 115 | Galb1-3(Fuca1-4)GlcNAcb1-3Galb1-4(Fuca1-3)GlcNAcb-Sp0 | 75 | 17 |
| 138 | Galβ1-4(Fucα1-3)GlcNAcβ1-4Galβ1-4(Fucα1-3)GlcNAcβ1-4Galβ1-4(Fucα1-3)GlcNAcβ–Sp0 | 74 | 27 |
| 21 | β-GlcNAc–Sp0 | 74 | 20 |
| 122 | Galb1-3(Neu5Aca2-6)GalNAca-Sp8 | 73 | 37 |
| 56 | Fuca1-2Galb1-3GalNAcb1-3Gala1-4Galb1-4Glcb-Sp9 | 73 | 31 |
| 63 | Fucα1-2Galβ1-3GlcNAcβ–Sp0 | 72 | 26 |
| 143 | Galb1-4GlcNAcb1-3(Galb1-4GlcNAcb1-6)GalNAca-Sp8 | 72 | 32 |
| 227 | Neu5Aca2-3Galb1-4[6OSO3]GlcNAcb-Sp8 | 71 | 7 |
| 203 | NeuAca2-8NeuAca2-8NeuAca2-8NeuAca2-3(GalNAcb1-4)Galb1-4Glcb-Sp0 | 71 | 26 |
| 10 | α-GalNAc–Sp8 | 71 | 13 |
| 65 | Fuca1-2Galb1-4(Fuca1-3)GlcNAcb1-3Galb1-4(Fuca1-3)GlcNAcb-Sp0 | 70 | 23 |
| 169 | GlcNAcb1-4(GlcNAcb1-6)GalNAca-Sp8 | 70 | 22 |
| 94 | Galα1-2Galβ–Sp8 | 69 | 18 |
| 166 | GlcNAcb1-3Galb1-4GlcNAcb1-3Galb1-4GlcNAcb-Sp0 | 69 | 16 |
| 62 | Fucα1-2Galβ1-3GlcNAcβ1-3Galβ1-4Glcβ–Sp8 | 67 | 24 |
| 151 | Galβ1-4GlcNAcβ1-6GalNAcα–Sp8 | 67 | 38 |
| 69 | Fucα1-2Galβ1-4GlcNAcβ1-3Galβ1-4GlcNAc–Sp0 | 66 | 20 |
| 259 | Neu5Gca2-3Galb1-4(Fuca1-3)GlcNAcb-Sp0 | 66 | 15 |
| 189 | Mana1-2Mana1-2Mana1-3Mana-Sp9 | 66 | 22 |
| 111 | Galα1-4Galβ1-4Glcβ–Sp0 | 65 | 11 |
| 251 | Neu5Acα2-6Galβ–Sp8 | 65 | 16 |
| 84 | GalNAcα1-3(Fucα1-2)Galβ–Sp8 | 64 | 21 |
| 37 | [3OSO3]Galb1-4GlcNAcb-Sp8 | 64 | 15 |
| 127 | Galb1-3GalNAcb1-3Gala1-4Galb1-4Glcb-Sp0 | 64 | 24 |
| 158 | GlcNAcβ1-2Galβ1-3GalNAcα–Sp8 | 64 | 18 |

Figure 3C

| | | | |
|---|---|---|---|
| 141 | Galb1-4GalNAca1-3(Fuca1-2)Galb1-4GlcNAcb-Sp8 | 63 | 17 |
| 70 | Fuca1-2Galb1-4GlcNAcb1-3Galb1-4GlcNAcb1-3Galb1-4GlcNAcb-Sp0 | 63 | 25 |
| 14 | α-Neu5Ac–Sp8 | 63 | 11 |
| 74 | Fucα1-2Galβ–Sp8 | 63 | 9 |
| 201 | Neu5Acα2-3(Galb1-3GalNAcb1-4)Galb1-4Glcb-Sp0 | 63 | 29 |
| 109 | Galα1-4Galβ1-4GlcNAcβ–Sp0 | 63 | 20 |
| 50 | Mana1-3(Mana1-6)Manb1-4GlcNAcb1-4GlcNAcb-Gly | 62 | 20 |
| 76 | Fucα1-3GlcNAcβ–Sp8 | 62 | 16 |
| 152 | Galβ1-4GlcNAcβ–Sp0 | 62 | 19 |
| 142 | Galb1-4GalNAcb1-3(Fuca1-2)Galb1-4GlcNAcb-Sp8 | 61 | 26 |
| 258 | Neu5Gcα2-3Galb1-3GlcNAcb-Sp0 | 61 | 13 |
| 27 | [3OSO3][6OSO3]Galb1-4GlcNAcb-Sp0 | 61 | 11 |
| 104 | Galα1-3Galb1-3GlcNAcb-Sp0 | 61 | 19 |
| 13 | α-L-Rhα–Sp8 | 60 | 20 |
| 150 | Galβ1-4GlcNAcβ1-6(Galβ1-3)GalNAcα–Sp8 | 60 | 16 |
| 16 | b-Neu5Ac-Sp8 | 60 | 18 |
| 247 | Neu5Acα2-6Galb1-4GlcNAcb1-3Galb1-4(Fuca1-3)GlcNAcb1-3Galb1-4(Fuca1-3)GlcNAcb-Sp0 | 60 | 15 |
| 162 | GlcNAcb1-3Galb-Sp8 | 60 | 14 |
| 15 | Neu5Acα1-2–Sp82 | 60 | 13 |
| 117 | Galβ1-3(Fucα1-4)GlcNAc–Sp0 | 59 | 20 |
| 48 | 9NAcNeu5Acα-Sp8 | 59 | 11 |
| 121 | Galβ1-3(GlcNAcβ1-6)GalNAcα-Sp8 | 59 | 15 |
| 110 | Galα1-4Galβ1-4GlcNAcβ–Sp8 | 58 | 27 |
| 71 | Fucα1-2Galβ1-4GlcNAcβ–Sp0 | 58 | 17 |
| 35 | [3OSO3]Galb1-4[6OSO3]GlcNAcb-Sp8 | 58 | 14 |
| 190 | Mana1-2Mana1-3(Mana1-2Mana1-6)Mana-Sp9 | 57 | 17 |
| 93 | GalNAcβ1-4GlcNAcβ–Sp8 | 57 | 14 |
| 191 | Mana1-2Mana1-3Mana-Sp9 | 57 | 17 |
| 184 | GlcAb-Sp8 | 57 | 14 |
| 153 | Galβ1-4GlcNAcβ–Sp8 | 57 | 24 |
| 64 | Fucα1-2Galβ1-3GlcNAcβ–Sp8 | 57 | 17 |
| 108 | Galα1-4(Fucα1-2)Galb1-4GlcNAcb-Sp8 | 56 | 19 |
| 239 | Neu5Acα2-3Galβ1-4Glcβ–Sp0 | 56 | 30 |

Figure 3D

| | | | |
|---|---|---|---|
| 57 | Fucα1-2Galβ1-3(Fucα1-4)GlcNAcβ–Sp8 | 56 | 15 |
| 86 | GalNAcα1-3Galb–Sp8 | 56 | 12 |
| 9 | α-D-Man–Sp8 | 55 | 14 |
| 204 | Neu5Aca2-8Neu5Aca2-8Neu5Aca2-3(GalNAcb1-4)Galb1-4Glcb-Sp0 | 55 | 21 |
| 195 | Manα1-3(Manα1-6)Manα–Sp9 | 55 | 13 |
| 246 | Neu5Acα2-6Galβ1-4GlcNAcβ–Sp8 | 55 | 37 |
| 176 | GlcNAcb1-6Galb1-4GlcNAcb-Sp8 | 55 | 11 |
| 44 | [6OSO3]Galβ1-4GlcNAcβ–Sp8 | 54 | 20 |
| 254 | Neu5Acβ1-6GalNAcα–Sp8 | 54 | 22 |
| 7 | α-D-Gal–Sp8 | 54 | 23 |
| 199 | Man5-9mix-Asn | 54 | 17 |
| 209 | Neu5Aca2-3(GalNAcb1-4)Galb1-4GlcNAcb-Sp0 | 54 | 11 |
| 47 | [6OSO3]GlcNAcβ–Sp8 | 54 | 21 |
| 198 | Mana1-6(Mana1-3)Mana1-6(Mana1-3)Manb1-4GlcNAcb1-4 GlcNAcb-Asn | 54 | 16 |
| 106 | Galα1-3Galβ1-4Glcβ–Sp0 | 53 | 11 |
| 165 | GlcNAcb1-3Galb1-4GlcNAcb-Sp8 | 53 | 18 |
| 119 | Galβ1-3(Fucα1-4)GlcNAcβ–Sp8 | 52 | 19 |
| 92 | GalNAcβ1-4GlcNAcβ–Sp0 | 52 | 8 |
| 60 | Fucα1-2Galβ1-3GalNAcβ1-4(Neu5Acα2-3)Galβ1-4Glcβ-Sp9 | 52 | 15 |
| 160 | GlcNAcβ1-3(GlcNAcβ1-6)Galb1-4GlcNAcb–Sp8 | 51 | 19 |
| 17 | β-D-Gal–Sp8 | 51 | 15 |
| 197 | Manα1-6(Manα1-3)Manα1-6(Manα2Manα1-3)Manβ1-4GlcNAcβ1-4GlcNAcβ-Asn | 51 | 11 |
| 29 | [3OSO3]Galβ1-4(6OSO3)Glcβ–Sp0 | 50 | 17 |
| 131 | Galb1-3GlcNAcb1-3Galb1-4GlcNAcb-Sp0 | 50 | 9 |
| 90 | GalNAcb1-3Gala1-4Galb1-4GlcNAcb-Sp0 | 50 | 21 |
| 235 | Neu5Acα2-3Galβ1-4GlcNAcβ1-3Galβ1-4GlcNAcβ1-3GlcNAcβ–Sp0 | 49 | 17 |
| 149 | Galβ1-4GlcNAcβ1-3Galβ1-4Glcβ–Sp8 | 49 | 16 |
| 183 | GlcAa-Sp8 | 49 | 24 |
| 129 | Galβ1-3GalNAcβ1-4Galβ1-4Glcβ–Sp8 | 49 | 15 |
| 177 | Glcα1-4Glcβ–Sp8 | 49 | 18 |

Figure 3 E

| | | | |
|---|---|---|---|
| 196 | Manα1-3(Manα1-2Manα1-2Manα1-6)Manα-Sp9 | 48 | 10 |
| 31 | [3OSO3]Galβ1-3(Fucα1-4)GlcNAcβ–Sp8 | 48 | 16 |
| 126 | Galβ1-3GalNAcβ–Sp8 | 48 | 14 |
| 114 | Galβ1-2Galβ–Sp8 | 48 | 19 |
| 101 | Galα1-3GalNAcα-Sp8 | 48 | 13 |
| 252 | Neu5Acα2-8Neu5Acα-Sp8 | 48 | 22 |
| 168 | GlcNAcb1-4MDPLys (bacterial cell wall) | 47 | 8 |
| 262 | Neu5Gcα2-6GalNAcα–Sp0 | 47 | 11 |
| 154 | Galβ1-4Glcβ–Sp0 | 47 | 13 |
| 192 | Manα1-6(Manα1-2Manα1-3)Manα1-6(Manα2Manα1-3)Manb1-4GlcNAcb1-4GlcNAcb-Asn | 46 | 21 |
| 124 | Galb1-3(Neu5Aca2-6)GlcNAcb1-4Galb1-4Glcb-Sp10 | 46 | 11 |
| 244 | Neu5Aca2-6Galb1-4[6OSO3]GlcNAcb-Sp8 | 46 | 17 |
| 193 | Manα1-2Manα1-6(Manα1-3)Manα1-6(Manα2Manα2Manα1-3)Manβ1-4GlcNAcβ1-4GlcNAcβ-Asn | 45 | 7 |
| 156 | GlcNAca1-3Galb1-4GlcNAcb-Sp8 | 45 | 11 |
| 68 | Fucα1-2Galβ1-4(Fucα1-3)GlcNAcβ–Sp8 | 45 | 7 |
| 132 | Galβ1-3GlcNAcβ1-3Galβ1-4Glcβ–Sp10 | 45 | 13 |
| 241 | Neu5Acα2-6(Galβ1-3)GalNAcα–Sp8 | 45 | 12 |
| 95 | Gala1-3(Fuca1-2)Galb1-3GlcNAcb-Sp0 | 45 | 17 |
| 261 | Neu5Gcα2-3Galβ1-4Glcβ–Sp0 | 45 | 4 |
| 102 | Galα1-3GalNAcβ–Sp8 | 45 | 14 |
| 40 | [4OSO3]Galb1-4GlcNAcb-Sp8 | 44 | 21 |
| 125 | Galβ1-3GalNAcα-Sp8 | 44 | 13 |
| 202 | Neu5Acα2-3Galb1-3GalNAca-Sp8 | 44 | 11 |
| 147 | Galβ1-4GlcNAcβ1-3Galβ1-4GlcNAcβ–Sp0 | 44 | 15 |
| 23 | b-GlcN(Gc)-Sp8 | 44 | 10 |
| 49 | 9NAcNeu5Aca2-6Galb1-4GlcNAcb-Sp8 | 43 | 14 |
| 237 | Neu5Acα2-3Galβ1-4GlcNAcβ–Sp8 | 43 | 8 |
| 182 | G-ol-amine | 43 | 16 |
| 208 | Neu5Acα2-3(6-O-Su)Galβ1-4(Fucα1-3)GlcNAcβ–Sp8 | 43 | 16 |
| 200 | Manb1-4GlcNAcb-Sp0 | 43 | 13 |
| 164 | GlcNAcβ1-3Galβ1-4GlcNAcβ–Sp0 | 43 | 17 |

Figure 3 F

| | | | |
|---|---|---|---|
| 205 | Neu5Acα2-8Neu5Acα2-8Neu5Acα2-3Galβ1-4Glcβ–Sp0 | 43 | 10 |
| 217 | Neu5Acα2-3Galb1-3(Fucα1-4)GlcNAcβ–Sp8 | 43 | 13 |
| 173 | GlcNAcβ1-4GlcNAcβ1-4GlcNAcβ–Sp8 | 43 | 20 |
| 185 | GlcAb1-3Galb-Sp8 | 43 | 12 |
| 257 | Neu5Gcα2-3Galb1-3(Fuca1-4)GlcNAcb-Sp0 | 43 | 8 |
| 87 | GalNAcα1-4(Fucα1-2)Galb1-4GlcNAcb-Sp8 | 42 | 16 |
| 228 | Neu5Acα2-3Galβ1-4(Fucα1-3)(6OSO3)GlcNAcβ–Sp8 | 42 | 13 |
| 78 | Fucb1-3GlcNAcb-Sp8 | 42 | 7 |
| 45 | [6OSO3]Galb1-4[6OSO3]Glcb-Sp8 | 42 | 17 |
| 99 | Galα1-3(Fucα1-2)Galβ–Sp8 | 42 | 16 |
| 89 | GalNAcb1-3(Fuca1-2)Galb-Sp8 | 42 | 13 |
| 20 | β-GalNAc–Sp8 | 42 | 9 |
| 171 | (GlcNAcb1-4)₆β–Sp8 | 42 | 20 |
| 128 | Galb1-3GalNAcb1-4(Neu5Acα2-3)Galb-4Glcb-Sp0 | 42 | 16 |
| 242 | Neu5Acα2-6GalNAcα–Sp8 | 42 | 17 |
| 215 | Neu5Acα2-3GalNAcb1-4GlcNAcb-Sp0 | 41 | 13 |
| 123 | Galb1-3(Neu5Acb2-6)GalNAca-Sp8 | 41 | 13 |
| 85 | GalNAcα1-3GalNAcb–Sp8 | 41 | 11 |
| 12 | α-L-Fuc–Sp9 | 41 | 17 |
| 51 | GlcNAcb1-2Mana1-3(GlcNAcb1-2Mana1-6)Manb1-4GlcNAcb1-4GlcNAcb-Gly | 41 | 7 |
| 256 | Neu5Acβ2-6(Galβ1-3)GalNAcα–Sp8 | 40 | 12 |
| 213 | Neu5Acα2-3(Neu5Acα2-6)GalNAcα–Sp8 | 40 | 18 |
| 222 | Neu5Acα2-3Galb-Sp8 | 40 | 11 |
| 210 | Neu5Acα2-3(GalNAcb1-4)Galb1-4GlcNAcb-Sp8 | 40 | 9 |
| 255 | Neu5Acb2-6Galb1-4GlcNAcb-Sp8 | 39 | 8 |
| 167 | GlcNAcβ1-3Galβ1-4Glcβ–Sp0 | 39 | 15 |
| 58 | Fucα1-2Galβ1-3GalNAcα–Sp8 | 39 | 15 |
| 112 | Galα1-4GlcNAcb–Sp8 | 39 | 7 |
| 139 | Galβ1-4[6OSO3]Glcβ–Sp0 | 39 | 7 |
| 236 | Neu5Acα2-3Galβ1-4GlcNAcβ–Sp0 | 38 | 13 |
| 42 | [6OSO3]Galβ1-4Glcβ–Sp0 | 38 | 13 |
| 88 | GalNAcb1-3GalNAca-Sp8 | 38 | 16 |

Figure 3G

| | | | |
|---|---|---|---|
| 148 | Galβ1-4GlcNAcβ1-3Galβ1-4Glcβ–Sp0 | 38 | 18 |
| 52 | Galb1-4GlcNAcb1-2Mana1-3(Galb1-4GlcNAcb1-2Mana1-6)Manb1-4GlcNAcb1-4GlcNAcb-Gly | 37 | 12 |
| 230 | Neu5Acα2-3Galβ1-4(Fucα1-3)GlcNAcβ–Sp0 | 37 | 11 |
| 250 | Neu5Acα2-6Galβ1-4Glcβ–Sp8 | 37 | 19 |
| 39 | [4OSO3][6OSO3]Galb1-4GlcNAcb-Sp0 | 37 | 12 |
| 221 | Neu5Acα2-3Galβ1-3(Neu5Acα2-6)GalNAcα–Sp8 | 37 | 10 |
| 206 | Neu5Acα2-8Neu5Acα2-3(GalNAcβ1-4)Galβ1-4Glcβ–Sp0 | 37 | 12 |
| 159 | GlcNAcβ1-3(GlcNAcβ1-6)GalNAcα–Sp8 | 37 | 12 |
| 53 | Neu5Aca2-3Galb1-4GlcNAcb1-2Mana1-3(Neu5Aca2-3Galb1-4GlcNAcb1-2Mana1-6)Manb1-4GlcNAcb1-4GlcNAcb-Gly | 36 | 17 |
| 98 | Gala1-3(Fuca1-2)Galb1-4Glcb-Sp0 | 36 | 10 |
| 214 | Neu5Acα2-3GalNAcα–Sp8 | 36 | 12 |
| 25 | (GlcNAcb1-3(GlcNAcb1-6)GlcNAcb1-4)GlcNAc-Sp8 | 35 | 8 |
| 231 | Neu5Acα2-3Galβ1-4(Fucα1-3)GlcNAcβ–Sp8 | 35 | 7 |
| 216 | Neu5Acα2-3Galβ1-3(6OSO3)GlcNAc-Sp8 | 34 | 17 |
| 77 | Fucα1-4GlcNAcβ–Sp8 | 34 | 11 |
| 146 | Galβ1-4GlcNAcβ1-3Galβ1-4GlcNAcβ1-3Galβ1-4GlcNAcβ–Sp0 | 34 | 9 |
| 161 | GlcNAcβ1-3GalNAcα–Sp8 | 34 | 9 |
| 22 | β-GlcNAc–Sp8 | 34 | 16 |
| 55 | Fuca1-2Galb1-3GalNAcb1-3Gala-Sp9 | 34 | 15 |
| 73 | Fucα1-2Galβ1-4Glcβ–Sp0 | 33 | 6 |
| 155 | Galβ1-4Glcβ–Sp8 | 32 | 6 |
| 79 | GalNAca1-3(Fuca1-2)Galb1-3GlcNAcb-Sp0 | 32 | 14 |
| 175 | GlcNAcβ1-6GalNAcα–Sp8 | 32 | 13 |
| 75 | Fuca1-2GlcNAcb-Sp8 | 32 | 11 |
| 170 | GlcNAcb1-4Galb1-4GlcNAcb-Sp8 | 32 | 12 |
| 211 | Neu5Acα2-3(GalNAcβ1-4)Galβ1-4Glcβ–Sp0 | 31 | 9 |
| 113 | Gala1-6Glcb-Sp8 | 31 | 10 |
| 32 | [3OSO3]Galβ1-3GalNAcα–Sp8 | 31 | 7 |

Figure 3 H

| | | | |
|---|---|---|---|
| 19 | β-D-Man–Sp8 | 31 | 7 |
| 248 | Neu5Acα2-6Galb1-4GlcNAcb1-3Galb1-4GlcNAcb-Sp0 | 31 | 16 |
| 220 | Neu5Acα2-3Galb1-3[6OSO3]GalNAcα-Sp8 | 30 | 6 |
| 194 | Manα1-2Manα1-2Manα1-3(Manα1-2Manα1-3(Manα1-2Manα1-6)Manα1-6)Manβ1-4GlcNAcβ1-4GlcNAcβ-Asn | 30 | 6 |
| 260 | Neu5Gcα2-3Galβ1-4GlcNAcβ–Sp0 | 30 | 10 |
| 186 | GlcAb1-6Galb-Sp8 | 30 | 11 |
| 91 | GalNAcb1-4(Fucα1-3)GlcNAcb-Sp0 | 30 | 11 |
| 263 | Neu5Gcα2-6Galβ1-4GlcNAcβ–Sp0 | 29 | 6 |
| 212 | NeuAcα2-3(NeuAcα2-3Galb1-3GalNAcb1-4)Galb1-4Glcb-Sp0 | 29 | 10 |
| 8 | α-D-Glc–Sp8 | 28 | 11 |
| 181 | Glcb1-6Glcb-Sp8 | 28 | 12 |
| 157 | GlcNAcα1-6Galb1-4GlcNAcb-Sp8 | 28 | 7 |
| 5 | Fibrinogen | 28 | 11 |
| 120 | Galβ1-3(Galβ1-4GlcNAcβ1-6)GalNAcα-Sp8 | 27 | 8 |
| 238 | Neu5Acα2-3Galb1-4GlcNAcb1-3Galb1-4GlcNAcb-Sp0 | 27 | 10 |
| 243 | Neu5Acα2-6GalNAcb1-4GlcNAcb-Sp0 | 27 | 14 |
| 249 | Neu5Acα2-6Galβ1-4Glcβ–Sp0 | 27 | 11 |
| 240 | Neu5Acα2-3Galβ1-4Glcβ–Sp8 | 26 | 11 |
| 174 | GlcNAcβ1-6(Galβ1-3)GalNAcα–Sp8 | 25 | 6 |
| 234 | Neu5Acα2-3Galb1-4GlcNAcb1-3Galb1-4(Fucα1-3)GlcNAc-Sp0 | 25 | 8 |
| 38 | [3OSO3]Galβ–Sp8 | 25 | 6 |
| 46 | NeuAcα2-3[6OSO3]Galβ1-4GlcNAcβ–Sp8 | 25 | 13 |
| 59 | Fucα1-2Galb1-3GalNAcb1-4(Neu5Acα2-3)Galb1-4Glcb-Sp0 | 25 | 9 |
| 41 | 6-H$_2$PO$_3$Manα–Sp8 | 23 | 6 |
| 226 | Neu5Acα2-3Galβ1-3GlcNAcβ–Sp8 | 23 | 11 |
| 180 | Glcb1-4Glcb-Sp8 | 22 | 8 |
| 245 | Neu5Acα2-6Galβ1-4GlcNAcβ–Sp0 | 22 | 5 |
| 232 | Neu5Acα2-3Galb1-4(Fucα1-3)GlcNAcb1-3Galb-Sp8 | 21 | 11 |
| 225 | Neu5Acα2-3Galβ1-3GlcNAcβ–Sp0 | 21 | 3 |
| 264 | Neu5Gcα–Sp8 | 21 | 12 |
| 207 | Neu5Acα2-8Neu5Acα2-8Neu5Acα-Sp8 | 20 | 8 |

Figure 3 I

| | | | |
|---|---|---|---|
| 61 | Fucα1-2Galβ1-3GlcNAcβ1-3Galβ1-4Glcβ–Sp10 | 19 | 8 |
| 178 | Glcα1-4Glca–Sp8 | 15 | 13 |
| 179 | Glcα1-6Glcα1-6Glcβ-Sp8 | 14 | 8 |
| 172 | (GlcNAcb1-4)$_5$β-Sp8 | 11 | 8 |

HIGH AFFINITY LIGANDS BIND TO CLOSTRIDIUM DIFFICILE TOXIN A

This application is a non-provisional of provisional Application Ser. No. 60/783,442 filed Mar. 20, 2006, the disclosure of which expressly incorporated herein.

TECHNICAL FIELD OF THE INVENTION

This invention is related to the area of gastrointestinal disease. In particular, it relates to disease caused by bacterial infection.

BACKGROUND OF THE INVENTION

*Clostridium difficile* is a Gram-positive spore forming organism that is a major cause of antibiotic-associated diarrhea (AAD) and pseudomembranous colitis (PMC). *C. difficile* was first isolated from the feces of patients undergoing clindamycin treatment in 1978 and identified as the pathogenic organism responsible for PMC (Larson 1978). *C. difficile* is an emerging pathogen responsible for severe gastrointestinal disease by production of potent toxins that damage the mucosal lining of the colon. Gastrointestinal infections range in severity from colonization to severe diarrhea, PMC, toxic megacolon, colonic perforation and death. The incidence of *C. difficile* infections in hospitalized patients has increased dramatically in recent years, with current incidence ranging from 2 to 30 cases per 1000 hospital admissions (Barbut, 2000, Johnson, 1990, Bartlett, 1992).

Conservative estimates place the cost of this disease in the U.S. alone at more than $1.1 billion per year. *C. difficile* infection increases hospital length of the stay by an average of 8 days and in geriatric patients by 36 days. An increasing proportion of patients present with life-threatening fulminant colitis. A recent study identified this incidence to be ~1.6% to 3.2% overall. Patients undergoing colectomy for *C. difficile* colitis had a mortality rate of 57%. (Dallal, 2002). be ~1.6% to 3.2% overall. Patients undergoing colectomy for *C. difficile* colitis had a mortality rate of 57%. (Dallal, 2002).

Current diagnosis is based on analysis of fresh diarrheic stools. The gold-standard is the cell-culture cytotoxin test, which detects toxin B by its effects on a cultured monolayer of human fibroblasts (Chang, 1979). A frequently used alternative is an antibody-based enzyme immunoassay test that directly identifies toxin A or both toxin A and B (Laughon, 1984). Endoscopic diagnosis of pseudomembranous colitis by the presence of characteristic white-yellowish plaques in the colon is a highly specific sign and pathognomonic of the disease (Fekety, 1993, Kelly, 1998).

Once diagnosed, conventional therapy involves reducing the predisposing conditions, (e.g., withdrawing the inciting antimicrobial therapy if possible), supportive therapy with intravenous fluids, and directed antimicrobial therapy with oral metronidazole (500 mg three times daily or 250 mg every 6 hrs) or oral vancomycin (125 mg every 6 hr). A typical duration of therapy is 10-14 days. Failure to respond (3-10%) may reflect the presence of ileitis or toxic megacolon, with both conditions preventing the drugs from reaching sufficient levels in the colon lumen and can require emergency surgical colostomy. Relapse following treatment is also common, occurring in 20-25% of cases (Mylonakis, 2001, McFarland, 1994). *C. difficile* infection can be a particular problem in immunodeppressed patients (e.g., transplant recipients and human immunodeficiency virus (HIV)-infected patients) who have higher rates of infection and significantly higher relapse rates. An emerging problem is the development of *C. difficile* isolates resistant to metronidazole and with intermediate resistance to vancomycin (Pelaez, 2002).

Most cases of *C. difficile* infection are acquired during hospitalization (nosocomial), although community-acquired cases are increasingly being reported (Hirschhorn, 1994, Kyne, 1998). As a spore-forming organism, *C. difficile* can persist as an infectious organism in a form that highly resistant to the action of disinfectants and can be recovered from almost every surface in the room of patients with *C. difficile* infection (Brazier, 1998, Nath, 1994). *C. difficile* spores are resistant to alcohol solutions routinely used for hand hygiene by health care providers. The ubiquitous presence of *C. difficile* spores is illustrated clearly by the fact that ~40% of the clinical recurrences are actually re-infections by a different strain (Alonso, 2001). *C. difficile* has also emerged as a significant pathogen of farm animals; causing an often-fatal hemorrhagic enteritis in foals, a nosocomial, antibiotic-associated disease in adult horses. Enteric disease is now recognized in ostriches, neonatal pigs, companion animals and calves. (Songer, 2004).

*Clostridium difficile* colonizes the colon of patients undergoing antibiotic therapy and produces two toxins responsible for the disease. These two toxins, TcdA and TcdB, are encoded on a pathogenicity locus. A critical role of toxin as the determinant of disease is supported by evidence: i) non-toxigenic strains are non-pathologic, ii) development of a strong antibody response reduces recurrence, and iii) the emerging clinical efficacy of toxin-binding resins.

Well-identified risk factors (e.g., use of an antimicrobial agent, advanced age, previous surgery and immunodepression, including transplantation and human immunodeficiency virus infection) underscore the need for novel agents or strategies directed toward prevention of primary infection/disease and post-treatment recurrence particularly attractive.

The clinical disease is believed to be primarily due to Toxin A, a tissue damaging enterotoxin. Toxin B is known to be a potent cytotoxin. Some evidence suggests that Toxins A and B act synergistically, with the initial tissue damage caused by Toxin A being necessary for Toxin B to exert its toxic effects. Therefore, although Toxin A is believed to cause most of the clinical symptoms, Toxin B may also play an important role in the disease. *C. difficile* is demonstrated in about 20% of antimicrobial-related diarrhea. The etiology of the remaining 80% of cases is still unknown (a potential role of other microorganisms, such as *Clostridium perfringens, Staphylococcus aureus* or *Candida albicans*, has been suggested).

Most cases of *C. difficile*-associated diarrhea (CDAD) are acquired in hospitals, although community-acquired cases are increasingly being reported. The most important risk factor for CDAD is the use of an antimicrobial agent during the previous 18 weeks (90% of cases), even in the form of a single prophylactic dose. Almost any antimicrobial agent may cause CDAD, although the risk is claimed to be especially high after the administration of clindamycin. Other implicated drugs include ampicillin, amoxicillin and cephalosporins, quinalones, and others, including even vancomycin and metronidazole. Other risk factors for the development of CDAD include advanced age, previous surgery and immunodepression, including transplantation and human immunodeficiency virus infection. Accordingly, there is a great need for effective preventative strategies.

Healthy carriers of *C. difficile* should not receive antibiotic therapy. Drugs commonly used for the therapy of CDAD are metronidazole (oral or intravenous) and vancomycin (only oral or rectal). Indications for therapy are the detection of a toxin-producing *C. difficile* strain in a patient with disease (diarrhea, fever, leucocytosis or compatible findings on colonoscopy). The key elements of therapy are to reduce the predisposing conditions (withdraw of unnecessary antimicrobials), provide supportive therapy with fluids, avoidance of anti-peristaltic agents, treatment with effective antimicrobial therapy. Oral metronidazole (500 mg TID) or oral vancomycin (125 mg every 6 h) have response rates near 90%. No well-performed studies have established the optimal normal duration of therapy. Although unproven, some authors recommend longer therapy to avoid recurrence. A therapeutic response usually involves the resolution of fever on the first day and of diarrhea on the fourth or fifth day. Metronidazole is frequently preferred to vancomycin because of lower cost, and because it potentially avoids selection for vancomycin-resistant enterococci.

The most common complication of the treatment of CDAD is relapse (occurring in up to 20-25% of cases). Immunodepressed patients (transplant recipients and human immunodeficiency virus-infected patients) have a higher index of relapse. Relapse should be suspected when the symptoms reappear after completion of therapy. The majority of relapses respond to another 10-day course of therapy with the same antimicrobial agent. However, 35% of patients may have subsequent relapses. These cases represent a major clinical problem. The optimal approach, a longer duration of antibiotic therapy, the use of pulses of vancomycin (125 mg/day), or the administration of resins to absorb the toxins (4 g of colestyramine BID), the use of probiotics (*Saccharomyces boulardii* or *Lactobacillus*) or the administration of intravenous immunoglobulins have all been proposed. Forty percent of clinical recurrences may actually reflect re-infections by a different strain. This suggests that these patients are exquisitely susceptible to reinfection.

The prevention and control of CDAD include: (i) the judicious use of antibiotics; (ii) contact precautions; and (iii) adequate environmental cleaning. Restriction of antimicrobial usage is a measure of proven efficacy in decreasing the incidence of CDAD. Accordingly the Department of Health and Public Health Laboratory Service Joint Working Party (1994) recommended: (i) written guidelines on correct antimicrobial use; (ii) restriction of susceptibility reports by the microbiology laboratory; (iii) programs of continuous medical education for healthcare workers; (iv) control and restriction of antimicrobial agent prescriptions; (v) automatic dates for termination of therapy; (vi) contact with the microbiologist or infectious disease specialist in special situations; (vii) avoidance of unnecessary use of antimicrobial agents; (viii) avoidance of wide-spectrum antimicrobial agents when feasible; (ix) avoidance of the use of antimicrobial agents especially linked to a high-risk of CDAD; (x) strict control of surgical prophylaxis.

Necessary first steps in the pathogenesis of disease are an antecedent disruption of the normal colonic flora followed by exposure to a toxigenic strain of *C. difficile*. Mechanistic steps following exposure include: i) ingestion of spores, ii) survival in the GI tract, iii) spore germination in the small bowel, iv) expansion and growth of toxigenic *C. difficile*, v) effective colonization and competition with commensal organisms, vi) possible adhesion, vii) toxin elaboration, and viii) binding and acting on epithelial cells.

The ability of *C. difficile* to form spores is thought to be a key feature that enables it to persist in patients and the physical environment for long periods—thereby facilitating hospital transmission. *C. difficile* is transmitted through the fecal-oral route. Based on animal models, most ingested vegetative cells are killed in the stomach, with only 1% of the inoculum passing into the small bowel. This may explain the association with potent acid suppressive therapies, such as proton pump inhibitors. *C. difficile* spores are acid resistant and pass through the stomach. Spores may germinate in the small bowel upon exposure to bile acids. A number of virulence factors, including flagellae and hydrolytic enzymes produced by the organism, have been associated with the development of disease. Nevertheless, the best characterized and most important virulence factors are the *C. difficile* exotoxins, toxins A and B Only toxigenic strains are associated with the development of *C. difficile* diarrhea. Toxin A is thought to play a more critical role than toxin B in the pathogenesis of *C. difficile* diarrhea because only it is associated with extensive tissue damage and fluid accumulation in experimental animal models. Toxin B, on the other hand, lacks direct enterotoxic activity and may play a role only after the gastrointestinal wall has been damaged by toxin A. However, toxin A-negative/toxin B-positive virulent *C. difficile* strains have been described, demonstrating that toxin A is not absolutely essential for virulence.

The key involvement of toxin A in most cases of disease have led to strategies designed to bind toxin released in the gut before it can interact with the epithelial receptor. A phase 2 study of the toxin-binding polymer tolevamer in patients with *C. difficile* associated diarrhea was presented demonstrating that tolevamer and vancomycin have similar efficacy in the treatment of mild-moderate CDAD. This randomized, double-blind, double-dummy, active-controlled phase 2 trial compared the safety and efficacy of monotherapy with 1 g or 2 g tolevamer TID versus a standard oral dose of 125 mg vancomycin QID in 289 patients with a first episode or recurrent CDAD. There was no statistically significant difference between vancomycin and 6 g tolevamer in either primary or recurrent CDAD patients. In the per protocol population, the definitive recurrence rate confirmed by a positive toxin assay was 19% with vancomycin and 10% with 6 g tolevamer (not statistically significant (p=0.185). In the per protocol population with recurrent CDAD at enrollment, the definitive recurrence rate was 27% with vancomycin and 0% with 6 g tolevamer (p=0.07). Others have produced and tested an injectable vaccine containing inactivated *C. difficile* toxins A and B. Four doses of this toxoid vaccine was shown to be immunogenic and well tolerated in a Phase I clinical study. This approach is currently being tested in clinical trials.

Hospitals and long-term care facilities are major reservoirs of *C. difficile* infection. Infected patients with diarrhea release *C. difficile* organisms and microscopic spores that persist in the environment for years. There is currently no effective method to prevent the transmission of *C. difficile* spores in healthcare facilities. Consequently, *C. difficile* outbreaks are frequent and can lead to the temporary closure of hospital units. At most, 8% of adults in the community are colonized with *C. difficile*. Once hospitalized, the risk of becoming colonized with *C. difficile* is proportional to the length of stay. Twenty percent of patients will become colonized after two weeks of hospitalization, and up to 50% will be colonized after being hospitalized for four weeks. This increase is presumed to be due to exposure to *C. difficile* in the hospital environment.

Considerable data demonstrate the potential therapeutic role of binding toxin to prevent interaction with physiologic receptors on the epithelial cell surface. Nilsson et al (Bioconjug Chem. 1997 8(4):466-71) showed the utility of solid supports for toxin neutralization. They immobilized enzymatically synthesized alpha Gal(1-3) beta Gal(1-4)Glc trisaccharide, producing a support that efficiently neutralized *Clostridium difficile* toxin A. The results from this study show that solid supports have potential to serve as inexpensive therapeutics for bacterial diseases mediated by toxin secreted into the lumen. A follow-up study (Gastroenterology. 1996 August;111(2):433-8) showed that pretreatment of rats by gavage dramatically reduced toxin A-associated fluid secretion and permeability. Braunlin et al (Biophys J. 2004 July; 87(1):534-9) demonstrated the utility of tolevamer, (GT160-246), a sodium salt of styrene sulfonate polymer, to inhibit the biological activity of *C. difficile* toxins.

There is a continuing need in the art to develop treatment protocols and reagents to prevent or ameliorate the effects of *C. difficile* infection.

SUMMARY OF THE INVENTION

One embodiment of the invention is a method of treating a mammal to reduce symptoms or to delay onset of *Clostridium difficile* infection or to reduce or prevent *Clostridium difficile* mediated intestinal damage. An oligosaccharide is administered to a mammal. The oligosaccharide comprises a structure galactose-β-1-3-N-acetyl-D-glucosamine-β-1-3-galactose-β-1-4-N-acetyl-D-glucosamine and optionally comprises one or more side chains. The oliogosaccharide may be in free form or attached to a non-absorbable polymer.

Another embodiment of the invention is a method of treating a mammal to reduce symptoms or to delay onset of *Clostridium difficile* infection or to reduce or prevent *Clostridium difficile* mediated intestinal damage. An oligosaccharide is administered to a mammal. The oligosaccharide comprises a structure galactose-α-1-3-galactose-β-1-4-N-acetyl-D-glucosamine and comprises one or more side chains. The oliogosaccharide may be in free form or attached to a non-absorbable polymer.

Also provide by the present invention is a pharmaceutical composition. The composition comprises a pharmaceutically acceptable carrier and an agent comprising an oligosaccharide having a structure galactose-β-1-3 N-acetyl-D-glucosamine-β-1-3-galactose-β-1-4-N-acetyl-D-glucosamine. The oligosaccharide optionally comprises one or more side chains. The oliogosaccharide may be in free form or attached to a non-absorbable polymer.

Also provide by the present invention is a pharmaceutical composition. The composition comprises a pharmaceutically acceptable carrier and an agent comprising an oligosaccharide having a structure galactose-α-1-3-galactose-β-1-4-N-acetyl-D-glucosamine. The oligosaccharide comprises one or more side chains. The oliogosaccharide may be in free form or attached to a non-absorbable polymer.

These and other embodiments which will be apparent to those of skill in the art upon reading the specification provide the art with treatment protocols and reagents for treating or preventing symptoms of *C. difficile* infection.

BRIEF DESCRIPTION OF THE DRAWINGS

FIG. 1 shows structures of ligands schematically. Binding activity is indicated in boxes as RLU.

FIG. 2 lists identifying numbers and structures of glycan ligands which bind Toxin A and the binding activity in the assay (RLU).

FIGS. 3A-3I list identifying numbers and structures of glycan ligands which do not appreciably bind Toxin A and the binding activity in the assay (RLU).

DETAILED DESCRIPTION OF THE INVENTION

It is a discovery of the present invention that certain oligosaccharides are able to bind to *Clostridium difficile* toxin A with higher affinity than previously known for other substances. Weaker binders are known in the art and have been found to alleviate, reduce, ameliorate, inhibit or prevent the biological effects of toxin A. The oligosaccharides which bind tighter can be used similarly.

Oligosaccharides of the invention can be used in the free form or can be bound or conjugated to larger polymers. For example, the oligosaccharides can be bound to non-absorbable polymers which do not leave the gastrointestinal lumen, but remain in the lumen until excreted. Many such non-absorbable polymers are known in the art and any can be used as is convenient. For example, surface-treated, calcined, diatomaceous earth (CHROMOSORB-P™) can be used as a solid support to which the oligosaccharides of the present invention can be bound or attached. For attachment, the product can be silylaminated and then chain-extended glycosylamide linkages can be coupled to the silylaminated product. See Nilsson, 1997. Another polymer which can be used is polystyrene sulfonate. This polymer demonstrates binding to toxins A and B on its own. The oliogosaccharides of the present invention can be bound or coupled to this polymer and the affinity of the polymer enhanced. Another polymer which can be used is cholestyramine, a cationic resin that has been used as a bile acid sequestrant.

Side chains which may be added to the oligosaccharide backbone according to the present invention include fucose, galactose, glucose, mannose, N-acetylneuraminic acid, N-acetyl-D-glucosamine, D-acetyl-D-glactosamine, and short chains of two or more identical or different moieties. Other saccharides which can be used according to the invention include glusoamine, galactosamine, N-acetylmuramic acid, N-acetylneuraminic acid, rhamnose, 2-deooxy-D-ribose, mannitol, inositol, gluconic acid, glucaric acid, gluconolactone, glucuronololactone, ascorbic acid, glucuronic acid, dehydroascorbic acid, fructose, xylose, and arabinose.

Oligosaccharides of the present invention can be administered per os or per anus to a mammal. The mammal may be a farm animal, such as an ostrich, chicken, turkey, cow, horse, pig. The mammal can be a companion animal such as a cat or a dog. The mammal can be a human. The oligosaccharides can be delivered before or after symptoms are noted. Mammals which are at risk of developing *C. difficile* infection can be treated in a prophylactic mode. This will reduce the severity, delay, or prevent the development of symptoms. Mammals are at elevated risk of infection if they are hospitalized, antibiotic treated, especially clindamycin treated, a transplant recipient, HIV-infected, or immunosuppressed.

Oligosaccharides of the present invention can also be used diagnostically. Binding can be used to determine whether symptoms present in a mammal are caused by *C difficile* infection.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

The active agents may also be formulated in rectal compositions such as suppositories or retention enemas, e.g., containing conventional suppository bases such as cocoa butter or other glycerides.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

Example 1

Introduction

Previous work showed that of *C. difficile* toxin A binds to carbohydrates that contain Gal alpha 1-3Gal beta 1-4GlcNAc. Since unsubstituted Gal alpha 3Gal beta 4GlcNAc beta sequences are not found in human tissues (due to suppression of the gene coding for the human enzyme Gal beta 3-transferase,) we reasoned that the actual physiologic target of toxin A must represent another oligosaccaharide. Accordingly, our study was undertaken to identify other oligosaccharide structures bound by toxin A. Binding to Gal alpha 3Gal beta 4GlcNAc beta-terminated glycosphingolipids of rabbit erythrocytes has also been demonstrated by Teneberg et al. Additional binding-active glycosphingolipids included GalNAc beta 3Gal beta 4GlcNAc beta 3Gal beta 4Glc beta 1Cer, GalNAc alpha 3Gal beta 4GlcNAc beta 3Gal beta 4 Glc beta 1 Cer, GalNAc alpha 3 (Fuc alpha 2) Gal beta 4GlcNAc beta 3Gal beta 4Glc beta 1 Cer, and GlcNAc beta 3 Gal beta 4 GlcNAc beta 3 Gal beta 4 Glc beta 1 Cer.

Example 2

Glycan Array Fabrication and Glycan Array Analyses

To define the carbohydrate binding specificity of *C. difficile* toxin A, we utilized a glycan microarray constructed by using standard robotic microarray printing technology containing amine functionalized glycans coupled to an amino-reactive glass slide at the Consortium for Functional Glycomics (see website at functionalglycomics.org). This array comprises over 260 synthetic and natural glycan sequences representing major glycan structures of known glycoproteins and glycolipids spotted in multiple replicates. Microarrays were printed as described in Blixt et al. Purified *Clostridium difficile* toxin A was applied to the slide at 200 micrograms/ml and incubated under a microscope cover-glass in a humidified chamber for 30 to 60 min. Unbound material was washed away, and bound toxin A was detected with mouse anti-*C. difficile* toxin A monoclonal antibody, PCG4 (10 ug/ml; available from GeneTex). Secondary Goat anti-mouse antibody-Alexa488 (10 ug/ml) was then applied. Following washing, fluorescence signals were analyzed using a confocal scanner (ScanArray 5000, PerkinElmer). Image analyses were carried out by using IMAGENE image analysis software (BioDiscovery, El Segundo, Calif.). Data were analyzed and plotted using Microsoft EXCEL software.

Example 3

Results

Figure 1:
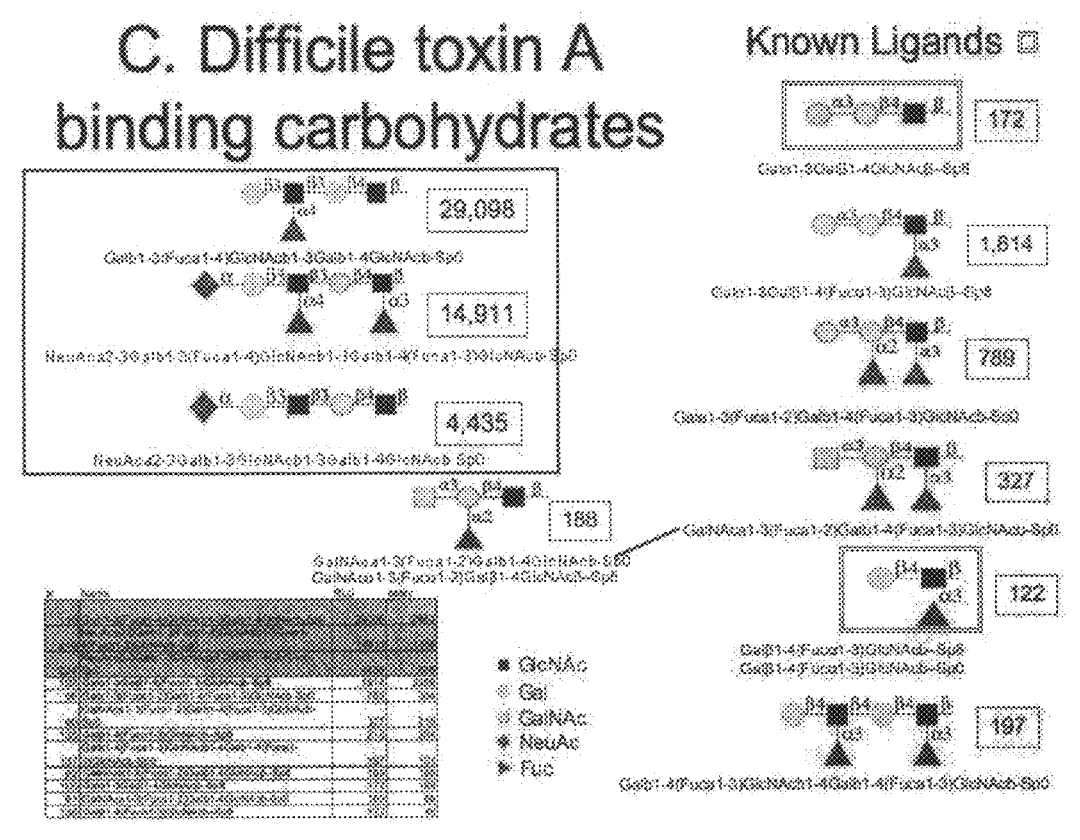

*C. difficile* toxin A has previously been documented to recognize a carbohydrate antigen, Lewisx(Galb1-4[Fuca1-3] GlcNAcb) (Infection and Immunity 59:73-8, 1991) and (Galb1-3Galb1-4GlcNAcb) (Biochem Cong. 8:466-71, 1997). Please refer to FIG. 1. Binding to these carbohydrate structures was demonstrated in our system, albeit weak, with fluorescence (FL) signals of 122/218 and 172 respectively. However, our analysis also demonstrated a number of more complex structures, with greater relative affinities; Gala1-3Galb1-4(Fuca1-3)GlcNAcb-(FL 1814), Gala1-3(Fuca1-2)Galb1-4(Fuca1-3)GlcNAcb-(FL 789), GalNAca1-3(Fuca1-2)Galb1-4(Fuca1-3)GlcNAcb-(FL 327), and GalNAca1-3(Fuca1-2)Galb1-4GlcNAcb-(FL 188). Each of these oligosaccharides bound toxin more strongly than the previously identified structures. These results support the importance of alpha 2 or 3 linked fuc and also demonstrate that GalNAca1-3 can substitute for Galb1-3 on the Galb1-3Galb1-4GlcNAcb backbone.

The array binding study also identified a completely new and previously unappreciated oligosaccharide motif bound by *C. difficile* toxin A. Galb1-3(Fuca1-4)GlcNAcb1-3Galb1-4GlcNAcb-(FL 29098), NeuAca2-3Galb1-3(Fuca1-4)GlcNAcb1-3Galb1-4(Fuca1-3)GlcNAcb-(FL 14911), and NeuAca2-3Galb1-3GlcNAcb1-3Galb1-4GlcNAcb-(FL 4435) were also identified. This supports the core Galb1-3GlcNAcb1-3Galb1-4GlcNAcb-backbone as a significantly stronger target of toxin A. The strongest signals were associated with Galb1-3(Fuca1-4)GlcNAcb1-3Galb1-4GlcNAcb-, and NeuAca2-3Galb1-3(Fuca1-4)GlcNAcb1-3Galb1-4(Fuca1-3)GlcNAcb-supporting the important contribution of alpha linked fucose to binding affinity.

REFERENCES

The disclosure of each reference cited is expressly incorporated herein.
1. Larson H E, Price A B, Honour P, Borriello S P. *Clostridium difficile* and the aetiology of pseudomembranous colitis. Lancet 1978; 1(8073): 1063-1066.
2. Barbut F, Petit J C. [Epidemiology, risk factors and prevention of *Clostridium difficile* nosocomial infections]. Pathol Biol (Paris) 2000; 48(8): 745-755.
3. Johnson S, Clabots C R, Linn F V, Olson M M, Peterson L R, Gerding D N. Nosocomial *Clostridium difficile* colonisation and disease. Lancet 1990; 336(8707): 97-100.
4. Bartlett J G. Antibiotic-associated diarrhea. Clin Infect Dis 1992; 15(4): 573-581
5. Dallal R M, Harbrecht B G, Boujoukas A J et al. Fulminant *Clostridium difficile*: an underappreciated and increasing cause of death and complications. Ann Surg 2002; 235(3): 363-372
6. Chang T W, Lauermann M, Barlett J G. Cytotoxicity assay in antibiotic-associated colitis. J Infect Dis 1979; 140: 765-770
7. Laughon B E, Viscidi R P, Gdovin S L, Yolken R H, Bartlett J G. Enzyme immunoassays for detection of *Clostridium difficile* toxins A and B in fecal specimens. J Infect Dis 1984; 149(5): 781-788
8. Fekety R, Shah A B. Diagnosis and treatment of *Clostridium difficile* colitis. J Am Med Assoc 1993; 269(1): 71-75
9. Kelly C P, LaMont J T. *Clostridium difficile* infection. Annu Rev Med 1998; 49: 375-390
10. Mylonakis E, Ryan E T, Calderwood S B. *Clostridium difficile* associated diarrhea: a review. Arch Intern Med 2001; 161(4): 525-533
11. McFarland L V, Surawicz C M, Greenberg R N et al. A randomized placebo-controlled trial of *Saccharomyces boulardii* in combination with standard antibiotics for *Clostridium difficile* disease. J Am Med Assoc 1994; 271(24): 1913-1918
12. Pelaez T, Alcala L, Alonso R, Rodriguez-Creixems M, Garcia-Lechuz J M, Bouza E. Reassessment of *Clostridium difficile* susceptibility to metronidazole and vancomycin. Antimicrob Agents Chemother 2002; 46(6): 1647-1650.
13. Hirschhorn L R, Trnka Y, Onderdonk A, Lee M L, Platt R. Epidemiology of community-acquired *Clostridium difficile*-associated diarrhea. J Infect Dis 1994; 169(1): 127-133.
14. Kyne L, Merry C, O'Connell B, Keane C, O'Neill D. Community-acquired *Clostridium difficile* infection. J Infect 1998; 36(3): 287-288
15. Brazier J S. The epidemiology and typing of *Clostridium difficile*. J Antimicrob Chemother 1998; 41(suppl C): 47-57.
16. Nath S K, Thomley J H, Kelly M et al. A sustained outbreak of *Clostridium difficile* in a general hospital: persistence of a toxigenic clone in four units. Infect Control Hosp Epidemiol 1994; 15(6): 382-389
17. Alonso R, Gros S, Pelaez T, Garcia-de-Viedma D, Rodriguez-Creixems M, Bouza E. Molecular analysis of relapse vs re-infection in HIV-positive patients suffering from recurrent *Clostridium difficile* associated diarrhea. J Hosp Infect 2001; 48(2): 86-92
18. Songer J G. The emergence of *Clostridium difficile* as a pathogen of food animals. Anim Health Res Rev. 2004 Dec;5(2):321-6.
19. Nilsson U J, Heerze L D, Liu Y C, Armstrong G D, Palcic M M, Hindsgaul O. Bioconjug Chem. 1997 July-August; 8(4):466-71. Immobilization of reducing sugars as toxin binding agents.
20. Braunlin W, Xu Q, Hook P, Fitzpatrick R, Klinger J D, Burrier R, Kurtz C B. Biophys J. 2004 July;87(1):534-9. Toxin binding of tolevamer, a polyanionic drug that protects against antibiotic-associated diarrhea.
21. Castagliuolo I, LaMont J T, Qiu B, Nikulasson S T, Pothoulakis C. Gastroenterology. 1996 Aug; 111(2):433-8. A receptor decoy inhibits the enterotoxic effects of *Clostridium difficile* toxin A in rat ileum.
22. Teneberg S, Lonnroth I, Torres Lopez J F, Galili U, Halvarsson M O, Angstrom J, Karlsson KA. Glycobiology. 1996 September;6(6):599-609. Molecular mimicry in the recognition of glycosphingolipids by Gal alpha 3 Gal beta 4 GlcNAc beta-binding *Clostridium difficile* toxin A, human natural anti alpha-galactosyl IgG and the monoclonal antibody Gal-13: characterization of a binding-active human glycosphingolipid, non-identical with the animal receptor.
23. Blixt, O, Head, S. Mondala, T. Scanlan, C Huflejt M. E. and Alvarez R. et al., Printed covalent glycan array for ligand profiling of diverse glycan binding proteins, Proc. Natl Acad. Sci. USA 101 (2004), pp. 17033-17038.

I claim:
1. A pharmaceutical composition comprising a pharmaceutically acceptable carrier and an agent, wherein the agent is glycan no. 116.
2. A pharmaceutical composition comprising a pharmaceutically acceptable carrier and an agent comprising an oligosaccharide, wherein the oligosaccharide consists of a structure galactose-$\beta$-1-3-[fucose-$\alpha$1-4]-N-acetyl-D-glucosamine-$\beta$-1-3-galactose-$\beta$-1-4-N-acetyl-D-glucosamine.
3. The pharmaceutical composition of claim 1 or 2 wherein the carrier is a liquid.
4. The pharmaceutical composition of claim 1 or 2 wherein the carrier is a solid.
5. The pharmaceutical composition of claim 1 or 2 further comprising a non-absorbable polymer.
6. The pharmaceutical composition of claim 2 wherein the oligosaccharide is attached to a non-absorbable polymer.
7. The pharmaceutical composition of claim 1 or 2 further comprising an antibiotic to which *Clostridium difficile* is sensitive.
8. The pharmaceutical composition of claim 7 wherein the antibiotic is metronidazole.
9. The pharmaceutical composition of claim 7 wherein the antibiotic is vancomycin.
10. A method to bind *Clostridium difficile* toxin A, comprising:
 administering to a mammal a pharmaceutical composition according to claim 1 or 2.
11. The method of claim 1 wherein the agent is covalently attached to a non-absorbable polymer.
12. The method of claim 1 wherein the mammal is a human.
13. The method of claim 1 wherein the mammal is a farm animal.
14. The method of claim 1 w herein the mammal is a companion animal.
15. The method of claim 1 wherein the mammal is infected with *C. difficile*.
16. The method of claim 1 wherein the mammal is at risk of infection with *C. difficile*.

17. The method of claim 1 wherein the agent is glycan no. 116.

18. The method of claim 12 wherein the human is hospitalized.

19. The method of claim 12 wherein the human is immunosuppressed.

20. The method of claim 12 wherein the human is a transplant recipient.

21. The method of claim 12 wherein the human is HIV positive.

22. The method of claim 12 wherein the human is or has been treated with clindamycin.

* * * * *

UNITED STATES PATENT AND TRADEMARK OFFICE
CERTIFICATE OF CORRECTION

PATENT NO. : 7,915,235 B2  
APPLICATION NO. : 11/716052  
DATED : March 29, 2011  
INVENTOR(S) : Dieckgraefe Page 1 of 1

It is certified that error appears in the above-identified patent and that said Letters Patent is hereby corrected as shown below:

In Column 10, Claim 11, Line 56
   Please remove "claim 1" and insert --claim 10--.

In Column 10, Claim 12, Line 58
   Please remove "claim 1" and insert --claim 10--.

In Column 10, Claim 13, Line 60
   Please remove "claim 1" and insert --claim 10--.

In Column 10, Claim 14, Line 62
   Please remove "claim 1" and insert --claim 10--.

In Column 10, Claim 15, Line 64
   Please remove "claim 1" and insert --claim 10--.

In Column 10, Claim 16, Line 66
   Please remove "claim 1" and insert --claim 10--.

In Column 11, Claim 17, Line 1
   Please remove "claim 1" and insert --claim 10--.

Signed and Sealed this
Thirty-first Day of May, 2011

David J. Kappos
*Director of the United States Patent and Trademark Office*